United States Patent [19]

Fujii, deceased et al.

[11] Patent Number: 5,185,337
[45] Date of Patent: Feb. 9, 1993

[54] PYRROLOQUINOLINE DERIVATIVES AND PHARMACEUTICAL COMPOSITIONS FOR ANTIMICROBIAL USE

[75] Inventors: Setsuro Fujii, deceased, late of Kyoto, by Keiko Fujii, Shinichiro Fujii, legal heirs; Kaoruko Takada, legal heir, Ehime; Hiroshi Ishikawa; Hidetsugu Tsubouchi, both of Shiga; Koichiro Jitsukawa, Hyogo, all of Japan

[73] Assignee: Otsuka Pharmaceutical Co., Ltd., Tokyo, Japan

[21] Appl. No.: 691,282

[22] Filed: Apr. 25, 1991

Related U.S. Application Data

[63] Continuation-in-part of Ser. No. 500,355, Mar. 28, 1990, abandoned.

[30] Foreign Application Priority Data

Mar. 29, 1989 [JP] Japan .................................. 1-78786
Sep. 28, 1990 [JP] Japan ................................ 2-262906

[51] Int. Cl.$^5$ .................... A61K 31/495; C07D 403/04
[52] U.S. Cl. ...................................... 514/254; 514/294; 544/229; 544/361; 546/13; 546/94
[58] Field of Search .......... 544/361; 546/94; 514/254, 294

[56] References Cited

FOREIGN PATENT DOCUMENTS 0390135 10/1990 European Pat. Off. .............. 546/94
56-30964 3/1981 Japan .
59-78189 5/1984 Japan ................................ 546/94
62-252790 11/1987 Japan .

Primary Examiner—C. Warren Ivy
Assistant Examiner—James H. Turnipseed

Attorney, Agent, or Firm—Sughrue, Mion, Zinn, Macpeak & Seas

[57] ABSTRACT

There is described pyrroloquinoline derivatives of general formula:

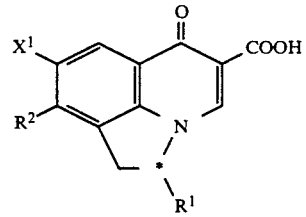

wherein R' is a $C_1$-$C_6$ alkyl group, $R^2$ is a group:

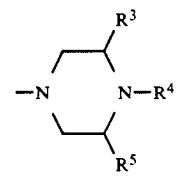

or group:

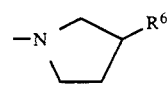

wherein $R^3$, $R^4$, $R^5$ and $R^6$ are as defined, or salt thereof. These compounds have an antimicrobial activity.

36 Claims, 2 Drawing Sheets

PYRROLOQUINOLINE DERIVATIVES AND PHARMACEUTICAL COMPOSITIONS FOR ANTIMICROBIAL USE

CROSS REFERENCE TO RELATED APPLICATION

This application is a continuation-in-part of Ser. No. 07/500,355 filed on Mar. 28, 1990, now abandoned.

FIELD OF THE INVENTION

This invention relates to pyrroloquinoline derivatives, process for preparing the same and pharmaceutical compositions for antimicrobial use.

BACKGROUND OF THE INVENTION

Various pyrroloquinoline derivatives are known which have antimicrobial activity. However, compounds which are more excellent in their antimicrobial activity are desired.

SUMMARY OF THE INVENTION

The main object of this invention is to provide pyrroloquinoline derivatives or salts thereof process for preparing the same having excellent antimicrobial activity and to provide a pharmaceutical compositions for antimicrobial use.

Namely, this invention provides pyrroloquinoline derivatives or thereof represented by the following general formula(I), which are optically active due to the asymmetric carbon atom at the 2-position.

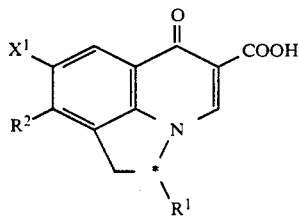

wherein $R^1$ is a $C_1$-$C_6$ alkyl group; $R^2$ is the group

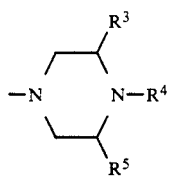

or the group

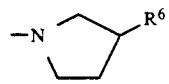

in which $R^3$, $R^4$ and $R^5$ are the same or different, each being either a hydrogen atom or a $C_1$-$C_6$ alkyl group, and $R^6$ is an amino group or a $C_1$-$C_6$ alkylamino-lower alkyl group; $X^1$ is a halogen atom; and * denotes the asymmetric carbon atom.

The compounds of this invention represented by the general formula (I) described above which are optically active due to the asymmetric carbon atom at the 2-position are so excellent in their antimicrobial activity that they are useful as antimicrobial compounds. In addition, the compounds (I) of this invention are characterized by low toxicity, long duration of effect, and good absorption when orally administered. The compounds (I) of this invention are particularly suitable for use in the form of injections because of their high solubility in water. Furthermore, the compounds (I) has low centric action.

The optically active compounds of this invention (I) are classified into two types described below.

(1) (+)-optically active compound:

The 2-position asymmetric carbon atom of pyrroloquinoline ring has the same configuration as the 2-position asymmetric carbon atom of indole ring in (−)-4,5-difluoro-2-methyl-1-[(S)-N-p-toluenesulfonyl-prolyl]-2,3-dihydroindole (Compound (a), $[\alpha]_D^{20} = -10.38°$ (c=1.06, chloroform)) described in Example 1.

The 2-position asymmetric carbon atom of the pyrroloquinoline ring has S-configuration, since it is confirmed by X-ray diffraction that the following (−)-optically active compound is R-configuration.

(2) (−)-optically active compound:

The 2-position asymmetric carbon atom of pyrroloquinoline ring has the same configuration as the 2-position asymmetric carbon atom of indole ring in (−)-4,5-difluoro-2-methyl-1-[(S)-N-p-toluenesulfonyl-prolyl]-2,3-dihydroindole (Compound (b), $[\alpha]_D^{20} = -71.84°$ (c=1.04, chloroform)) described in Example 1.

It is confirmed by X-ray diffraction that the 2-position asymmetric carbon atom of the pyrroloquinoline ring has R-configuration.

The compounds (a) and (b) described above are contained in the compounds of general formula (II) which are optically active.

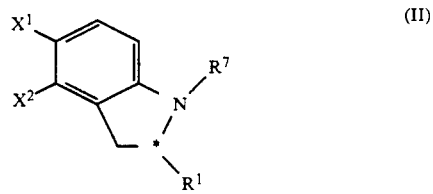

wherein $R^1$, $X^1$ and * have the same meanings as defined above; $X^2$ is a halogen atom; $R^7$ is a hydrogen atom or the group:

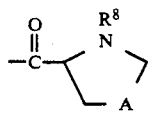

in which $R^8$ is a protective group; and A is a $C_1$-$C_6$ alkylene group.

The optically active compounds represented by the general formula (II) are useful as the intermediates for the synthesis of the compounds (I) of this invention.

In another aspect, this invention provides the pyrroloquinoline derivatives represented by the general formula (III).

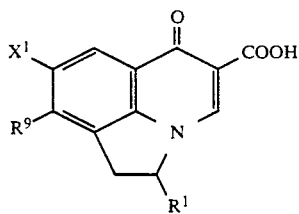

(III)

wherein $R^1$ and $X^1$ have the same meanings as defined above; $R^9$ is the group

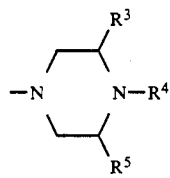

or the group

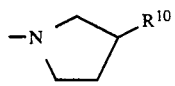

in which $R^3$, $R^4$ and $R^5$ have the same meanings as defined above, provided that $R^3$ and $R^5$ should not both be hydrogen atoms, and $R^{10}$ is a $C_1$-$C_6$ alkylamino-$C_1$-$C_6$ alkyl group. The pyrroloquinoline derivatives (III) are racemic modifications.

The pyrroloquinoline derivatives of the general formula (III) are excellent in their antimicrobial activity, and therefore useful as antimicrobial agents. The compounds (III) of this invention are characterized by low toxicity, long duration of effect, and good absorption when orally administered, further good solubility in water and low centric action.

In another aspect, this invention provides the pyrroloquinoline derivatives represented by the following general formula (IV).

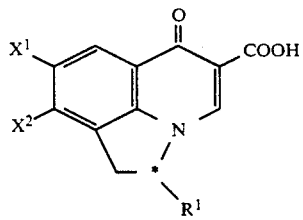

(IV)

wherein $R^1$, $X^1$, $X^2$ and * have the same meanings as defined above.

The pyrroloquinoline derivatives in this invention are useful as the intermediate for the salts which have good solubility in water. Hydrochloride, sulfate and methansulfonate are desirable as salt, and among them, hydrocholoride is especially desirable.

DETAILED DESCRIPTION OF THE INVENTION

The groups given in this specification are respectively described in more detail in the following.

The halogen atoms include fluorine, chlorine, bromine and iodine atoms and the like, among which fluorine and chlorine atoms are particularly desirable.

Examples of the $C_1$-$C_6$ alkyl groups include straight chain or branched alkyl groups, such as methyl, ethyl, propyl, isopropyl, butyl, tert-butyl, pentyl, hexyl and the like. Among these, methyl and ethyl are desirable, and methyl is particularly desirable.

Examples of the $C_1$-$C_6$ alkylamino-$C_1$-$C_6$ alkyl groups include alkylaminoalkyl groups of which alkyl moieties are straight chain or branched alkyls having 1 to 6 carbon atoms, such as methylaminomethyl, ethylaminoethyl, propylaminomethyl, isopropylaminomethyl, butylaminomethyl, pentylaminomethyl, hexylaminomethyl, methylaminopropyl, ethylaminobutyl, ethylaminopentyl, propylaminohexyl and the like.

Examples of the protective groups represented by $R^8$ include $C_1$-$C_6$ alkyl-substituted phenylsulfonyl groups, $C_1$-$C_6$ alkyl-substituted phenylcarbonyl groups or the like. The $C_1$-$C_6$ alkyl-substituted phenylsulfonyl group are exemplified by phenylsulfonyl groups substituted by straight chain or branched alkyl groups, such as p-toluensulfonyl group.

The $C_1$-$C_6$ alkyl-substituted phenylcarbonyl groups are exemplified by phenylcarbonyl groups substituted by straight chain or branched alkyl groups, such as 4-metylbenzoyl group.

Examples of the $C_1$-$C_4$ alkylene groups include straight chain or branched alkylene groups, such as metylene, etylene, trimetylene, tetrametylene and the like.

The compounds of this invention are the prepared for example according to the following reaction scheme.

[Reaction Scheme]

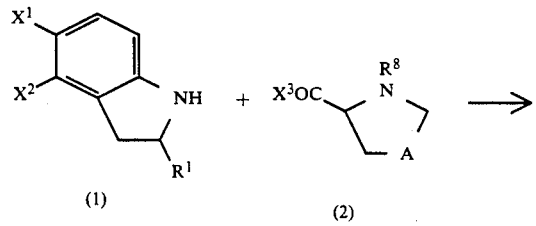

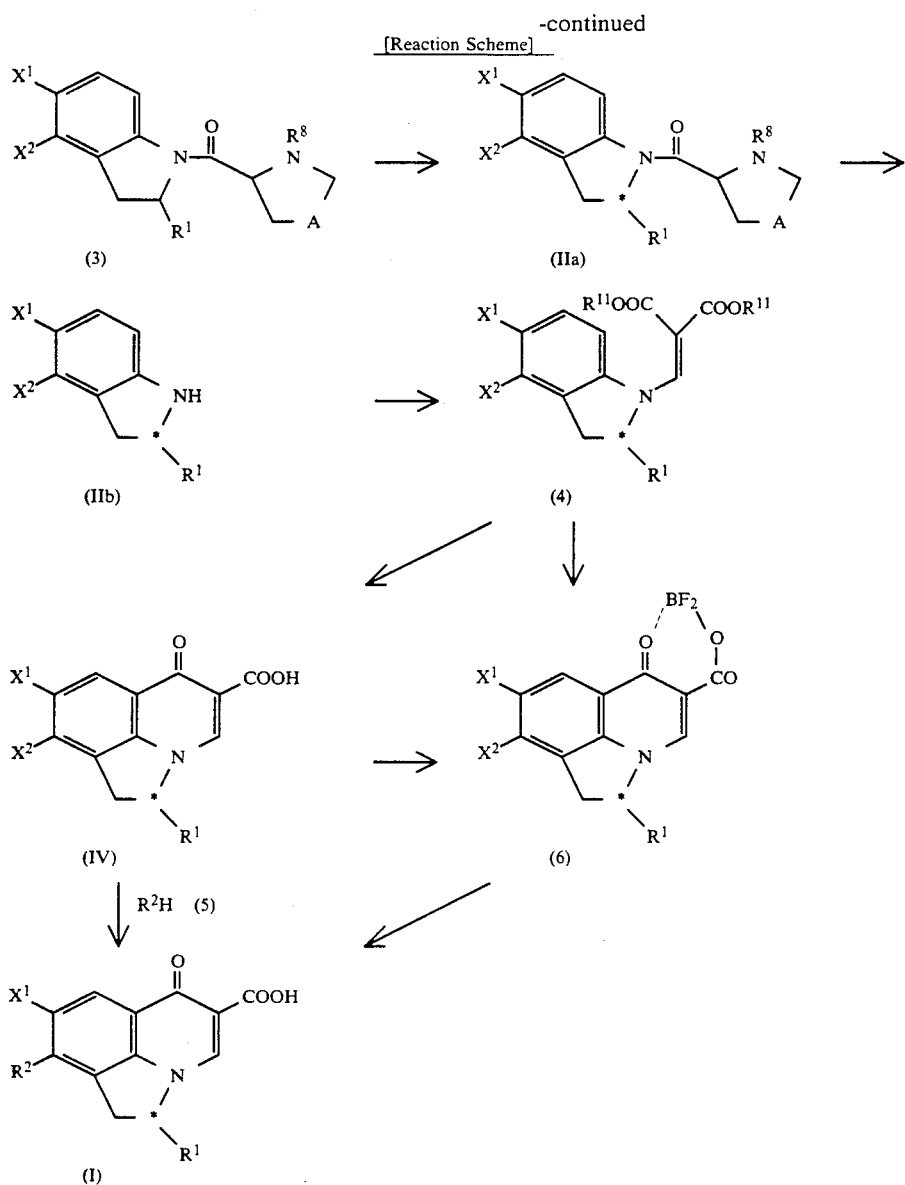

wherein $R^1$, $R^2$, $R^3$, $R^4$, $R^5$, $R^6$, $R^7$, $R^8$, $R^9$, $R^{10}$, $X^1$, $X^2$, A and * have the same meanings as defined above; $X^3$ is a hydroxyl group, a halogen atom or a reactive derivative residue of a carboxyl group; and $R^{11}$ is a $C_1$-$C_6$ alkyl group.

The reactive derivatives residues of carboxyl group represented by $X^3$ in the general formula shown above include active ester residues, acid anhydride residues and the like.

The condensation between the compound (1) and a cyclic amino acid or its reactive derivative (2) is carried out by any of the usual methods for amide bond-forming reaction (for example, the acid halide method, the active ester method, the acid anhydride method, the DCC method, etc.).

For example, according to the acid halide method, the compound (3) can be produced by reacting the racemic compound (1) with an acyl halide (2) wherein $X^3$ is a halogen atom in the presence of a deoxidizer in a suitable solvent.

The deoxidizers that can be used in this invention include sodium hydrogencarbonate, sodium carbonate, potassium carbonate, pyridine, triethylamine, etc. The solvents that can be used in this invention include benzene, halogenated hydrocarbons such as chloroform, methylene chloride and carbon tetrachloride, and ethers such as dioxane and tetrahydrofuran. The acyl halide (2) and the compound (1) are present at least in a molar ratio of about 1:1, preferably 1:1 to 3:1. The reaction is conducted usually at −30° C. to about 100° C., preferably room temperature to about 80° C., and completes in 20 minutes to 20 hours.

The optically active compound (IIa) can be separated from the compound (3) by fractional crystallization or chromatography on silica gel, or by combination thereof.

The configuration at the asymmeric carbon atom of the 2-position in the optically active compound (IIa) is the same S-configuration as that in the Compound (a) of Example 1 described below.

The compound (IIb) can be obtained by hydrolysis of the optically active compound (IIa) separated. The hydrolysis is conducted in a solvent in the presence of a catalyst conventionally used for hydrolysis. The catalysts for hydrolysis include basic compounds such as sodium hydroxide, potassium hydroxide, barium hydroxide, etc., mineral acids such as sulfuric acid, hydrochloric acid, nitric acid, etc., and organic acids such as acetic acid, aromatic sulfonic acid etc. The solvents include water, lower alcohols such as methanol, ethanol, isopropanol, etc., ketones such as acetone, metylethylketone, etc., ethers such as dioxane, dietylene glycol, etc., acetic acid, and so on. The reaction is carried out usually at room temperature to about 200° C., preferably at about 50° C. to about 150° C.

The compound (4) can be obtained by reacting the compound (IIb) with dialkylethoxymethylene malonate. The said reaction may be carried out either in the absence of a solvent or in the presence of a solvent, preferably in the absence of a solvent. The solvents that can be used in the reaction include aromatic hydrocarbons such as benzene, toluene, xylene, etc., acetonitrile, dimethylformamide, dimethyl sulfoxide, hexamethylphosphoric triamide, and so on. Dialkylethoxymethylene malonate and the compound (IIb) may be used usually in a molar ratio of 1:1 or more; in the reaction in the absence of a solvent the ratio is preferably 1:1 and in the reaction in a solvent the ratio is preferably about 1.1:1 to about 1.5:1. The reaction is carried out usually at room temperature to about 150° C., preferably at about 100°–130° C., and completes usually in about 0.5–6 hours.

The cyclization of the compound (4) can be conducted according to the known various cyclization procedures. In the concrete, as examples of the cyclization procedure, there may be mentioned cyclization by heating, and cyclization using an acidic substance such as phosphorus oxide chloride, phosphorus pentachloride, phosphorus trichloride, thionyl chloride, concentrated sulfuric acid, polyphosphoric acid etc. The cyclization by heating is carried out in a suitable solvent usually at about 100° C. to about 250° C., preferably about 150° C. to about 200° C. The solvents that can be used include hydrocarbons of high boiling point and ethers of high boiling point, such as tetralin, diphenyl ether, diethylene glycol, dimethyl ether, etc. In the cyclization using an acidic substance, equimolar amount to a large excess of the acidic substance is used for the amount of the compound (4), preferably 10 to 20 times moles of the acidic substance is used for a mole of the compound (4); the reaction is carried out usually at about 100° C. to about 150° C. and completes in about 0.5 to about 6 hours. The cyclization produces an ester derivative of the compound of the general formula (IV).

The compound (IV) can be produced by hydrolysis of the above-mentioned ester derivative described above in a solvent in the presence of a conventional catalyst for hydrolysis. As the catalysts and the solvents, those used for the hydrolysis of the optically active compound (IIa) described above can be used. The said reaction is usually carried out at room temperature to about 200° C., preferably about 50° C. to about 150° C.

The reaction between the compound (IV) and the compound (5) represented by the general formula $R^2H$ (wherein $R^2$ has the same meaning as defined above) is carried out in an inert solvent. As example of the said solvent there may be mentioned water, alcohols such as methanol, ethanol, isopropanol, butanol, amyl alcohol, isoamyl alcohol, etc., aromatic hydrocarbons such as benzene, toluene, xylene, etc., ethers such as tetrahydrofuran, dioxane, diglyme, etc., dimethyl sulfoxide, dimethylformamide, hexamethylphosphoric triamide, and so on. Among these solvents, dimethyl sulfoxide, dimethylformamide and hexamethylphosphoric triamide are particularly desirable. The molar ratio of the compound (IV) and the compound (5) is not specified and can be employed suitably from a wide range; for one mole of the compound (IV), usually 1 mole or more, preferably 1 mole to about 5 moles of the compound (5) is used. The said reaction is carried out usually at about 1 atm to about 20 atm, preferably at about 1 atm to 10 atm, and at about 50° C. to about 200° C., preferably at about 80° C. to about 150° C., and completes usually in about 1 hour to about 10 hours. This reaction may be carried out in the presence of a deoxidizer. As examples of the deoxidizer, there may be mentioned inorganic carbonates such as sodium carbonate, potassium carbonate, potassium hydrogencarbonate, sodium hydrogencarbonate, tertiary amines such as pyridine, quinoline, triethylamine, etc., and so on.

The compound (I) can also be produced by reacting the chelate compound (6) obtained either from the compound (4) or from the compound (IV), with the compound (5).

The reaction to obtain the chelate compound (6) is carried out by reacting the compound (4) or the compound (IV) with boron trifluoride or a complex thereof in an inert solvent. Complexes of boron trifluoride that can be used include ether complex, acetic acid complex, ketone complex, etc. Boron trifluoride or a complex thereof and the compound (4) or the compound (IV) are present usually in a molar ratio of 1:1 or more, preferably 1:1 to about 2:1. As examples of the inert solvent, there may be mentioned aromatic hydrocarbons such as benzene, toluene, xylene, etc., and ethers such as tetrahydrofuran, diethyl ether, etc. The reaction is carried out usually at about 100° C. to about 200° C., preferably at about 100° C. to about 150° C., and completes usually in about 3 hours to about 10 hours.

The reaction between the chelate compound (6) and the compound (5) is carried out in a similar manner as the reaction between the compound (IV) and the compound (5) described above. The said reaction is carried out usually at about 50° C. to about 150° C., preferably at about 50° C. to about 100° C., and completes usually in about 5 hours to about 20 hours.

Among the compounds represented by the formula (I) those wherein $R^2$ is

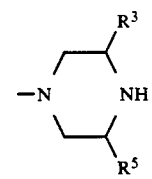

can be transformed into the compounds wherein $R^2$ is

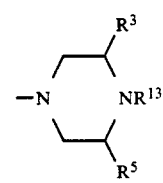

(in which $R^{13}$ means a $C_1$-$C_6$ alkyl group) by a known method for alkylati on. The methods for alkylation indlude (i) a method wherein a compound represented by the general formula $R^{13}X^4$ (in which $R^{13}$ is a $C_1$-$C_6$ alkyl group; $X^4$ is a halogen atom) is allowed to react in the presence of a deoxidizer, and (ii) a method wherein a lower alkanol is allowed to react in the presence of a reducing agent. For example, according to the method (ii), the reaction is carried out in the presence of a reducing agent in the absence of a solvent or in a suitable solvent. As examples of the reducing agent, there may be mentioned sodium formate-formic acid, sodium borohydride, lithium aluminum hydride, etc. As examples of the solvent there may be mentioned aromatic hydrocarbons such as benzene, toluene etc., halogenated hydrocarbons such as chloroform, methylene chloride, etc., ethers such as tetrahydrofuran, etc., and so on. This reaction is carried out usually at about 50° C. to about 200° C., preferably at about 50° C. to about 150° C., and completes usually in about 3 hours to about 10 hours.

Among the optically active compounds according to the present invention, those that can form salts can also be produced from the corresponding racemic compounds.

For example, the optically active compound (IIb) can be obtained from the racemic compound (1). Namely, the salt of the compound (1) is formed by reacting the compound (1) with an optically active compound, and subjected to fractional crystallization, followed by desalting of the resultant salt of the optically active compound (IIb), to give the compound (IIb).

As the optically active compound used for salt formation of the compound (1), a variety of known compounds may be used as far as they are optically active compounds that can form salts with the compound (1), including optically active acids such as (+)- and (−)-tartaric acid, (−)-malic acid, (−)-mandelic acid, and D- and L-camphor-10-sulfonic acid. Among these, D- and L-camphor-10-sulfonic acid is particularly desirable. As the solvent used for the salt-formation, any of those used for usual optical resolution can be used, including water, alcohols such as methanol, ethanol, isopropanol, etc., aromatic hydrocarbons such as benzene, toluene, xylene, etc., halogenated hydrocarbons such as dichloromethane, chloroform, carbon tetrachloride, etc., ethers such as tetrahydrofuran dioxane, diglyme, etc., aliphatic hydrocarbons such as n-hexane, n-heptane, cyclohexane, etc., polar solvents such as dimethyl sulfoxide, dimethylformaide, hexamethylphosphoric triamide, etc., and the mixtures thereof. The optically active compound and the compound (1) are present usually in a molar ratio of about 0.3:1 to about 3:1, preferably in a molar ration of about 0.5:1 to about 1:1. This reaction proceeds usually at about 0° C. to about 100° C., preferably at room temperature to about 50° C.

As the mentioned for fractional crystallization of the salt of the compound (1) formed as described above, any of the known methods can be employed.

Desalting of the salt of the compound (IIb) obtained by fractional crystallization is carried out in a suitable solvent in the presence of a basic compound. As the solvent that can be used here any of those used in the salt-formation described above may be used. As examples of the basic compound there may be mentioned inorganic salts such as sodium hydroxide, sodium carbonate, potassium hydroxide, potassium carbonate, potassium hydrogencarbonate, sodium hydrogencarbonate, etc. Desirably an excess of the basic compound is used.

All of the optically active compounds according to the present invention each of which has an asymmetric carbon at the 2-position have the same S-configuration at the 2-position as that in the compound (a) of Example 1 described below.

The compounds according to the present invention can be easily converted to acid adducts by permitting a pharmaceutically acceptable acid to act thereon. The acid is exemplified by inorganic acids such as hydrochloric acid, sulfuric acid, phosphoric acid, hydrobromic acid, etc., and organic acids such as oxalic acid, maleic acid, fumaric acid, malic acid, tataric acid, citric acid, benzoic acid, etc..

In addition, the compounds according to the present invention can be easily converted to salts by permitting a pharmaceutically acceptable basic compound to act thereon. The basic compound is exemplified by sodium hydroxide, potassium hydroxide, calcium hydroxide, sodium carbonate, potassium hydrogencarbonate, etc..

The thus-produced compound of this invention can be isolated from the reaction system and purified without difficulty by conventional means of separation such as distillation, recrystallization, column chromatography, preparative thin layer chromatography, and solvent extraction.

The compounds and the salts thereof represented by the general formula (I), (III) and (IV) according to the present invention are used as antimicrobial agents in the form of pharmaceutical preparations obtained by combining the compounds or the salts thereof with suitable pharmaceutically acceptable carriers. Any of the conventional carriers can be employed, including excipients, binders, lubricants, coloring agents, disintegrants, etc.

Various dosage forms of the antimicrobial agents can be selected according to the purpose of the therapy. In the concrete, the dosage forms include tablets, pills, powders, liquid preparations, suspensions, emulsions, granules, capsules, suppositories, and injectable preparations (solutions, suspensions, etc.), ointments, etc.

The compounds of this invention are used in the form of ordinary pharmaceutical preparations. The preparation is formulated by using diluents or excipients such as fillers, extenders, binders, wetting gents, disintegrants, surfactants, lubricants, etc. Various dosage forms of these pharmaceutical preparations can be selected according to the purpose of the therapy, and typical forms include tablets, pills, powders, suspensions, emulsions, granules, capsules, suppositories, injections (solutions, suspensions, etc.), ointments, and so on. In molding a pharmaceutical composition into a tablet form, examples of the carriers include excipients such as lactose, white sugar, sodium chloride, glucose, urea, starch, calcium carbonate, kaolin, crystalline cellulose, and silicic acid, binders such as water, ethanol, propanol, simple syrup, glucose solution, starch solution, gelatin solution, carboxymethlcellulose, shellac, methylcellulose, potassium phosphate and polyvinyl pyrrolidione, disintegrants such as dried starch, sodiym alginate, agar powder, laminaria powder, sodium hydrogencarbonate, calcium carbonate, polyo xyethylenesorbitan fatty acid esters, sodium laurylsulfate, stearic acid monoglyceride, starch, and lactose, disintegration inhibitors such as white sugar, stearin, cacao butter and hydrogenated oils, absorption promoters such as quaternary ammonium bases and sodium laurylsulfate, humectants such as glycerol and starch, adsorbents such as starch, lactose, kaolin, bentonite and colloidal silicic acid, and lubricants such as purified talc, stearic acid salts, boric acid powder, polyethylene glycol. The tablets, if desired, can be coated, and made into sugar-coated tablets, gelatin-coated tablets, enteric-coated tablets, film-coated tablets, or tablets comprising two or more layers.

In molding the pharmaceutical composition into pills, examples of the carriers include excipients such as glucose, lactose, starch, cacao butter, hardened vegetable oils, kaolin and talc, binders such as gum arabic powder, tragacanth powder, gelatin, and ethanol, and disintegrants such as laminaria and agar. In molding the pharmaceutical composition into a suppository form, examples of the carriers include polyethylene glycol, cacao butter, higher alcohols, esters of higher alcohols, gelatin, and semisynthetic glycerides. Capsules are prepared by filling the compounds of this invention mixed with various carriers described above as examples into hard gelatin capsules and soft capsules, according to the conventional procedure. When the pharmaceutical composition is formulated into an injectable preparation, the resultant solution, emulsion and suspension are sterilized, and are desirably isotonic with respect to the blood. In formulating, emulsion or suspension, examples of the diluents include water, aqueous solution of lactic acid, ethyl alcohol, propylene glycol, ethoxylated isostearyl alcohol, polyoxidized isostearyl alcohol, and polyoxyethylenesorbitan fatty acid esters. Sodium chloride, glucose or glycerol may be incorporated into a pharmaceutical composition, in an amount sufficient to prepare isotonic solutions. The pharmaceutical composition may further contain ordinary dissolving aids, buffers, painalleviating agents, and optionally coloring agents, preservatives, perfumes, flavors, sweeteners and other drugs. In molding a pharmaceutical composition into a paste form, a cream form, and a gel form, examples of the diluents include white petrolatum, paraffin, glycerin, cellulose derivatives, polyethylene glycol, silicones, and bentonite.

The amount of the compound of the present invention to be incorporated into a pharmaceutical composition is not particularly limited, and can be selected appropriately from a wide range, being usually about 1 to about 17% by weight.

The administration method of the pharmaceutical composition according to the invention is not particularly limited and can be adequately selected according to the form of the preparation, age, sex and other conditions of the patient, severity of the disease, etc.. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the injectable preparations can be singly administered intramuscularly, intracutaneously, subcutaneously, or intraperitoneally. The suppository is administered intraectally. The ointment is applied on the skin.

The dosage of the pharmaceutical composition is suitably selected according to the purpose of use, age, sex, and other conditions of the patient, and severity of the disease, etc.. Usually, the pharmaceutical composition containing a preferred dosage of the compound of this invention as the effective ingredient of about 10 mg/body to about 5 g/body may be administered by dividing into 3 to 4.

EXAMPLES

Hereinafter, Examples, Reference Example, Pharmacological Activity Test Example, and Pharmaceutical Examples are described.

EXAMPLE 1

($\pm$)-4,5-difluoro-2-methyl-2,3-dihydroindole, 47.4 g, was dissolved in 470 ml of methylene chloride, to which was added 45 ml of pyridine under ice-cooling. To the resultant mixture was added dropwise under ice-cooling 300 ml of a methylene chloride a solution of the acid chloride prepared from 98.8 g of (S)-N-p-toluenesulfonyl proline and 80 ml of thionyl chloride. After the dropwise addition, the reaction was conducted for 1.5 hours at room temperature. The reaction mixture was washed with 750 ml of 10% hydrochloric acid, with a saturated aqueous solution of sodium hydrogencarbonate, and with a saturated aqueous solution of sodium chloride, in this order, and dried over anhydrous magnesium sulfate. Methylene chloride was evaporated off, the residue was washed with ether, with benzene and with ethanol, in this order. All of the washings were combined and concentrated, and the residue was subjected to column chromatography on 3 kg of silica gel with elution with benzene-ethyl acetate (30:1-15:1), to give a main product and a by-product. The main product was recrystallized from isopropanol-benzene, to give 51.8 g of (−)-4,5-difluoro-2-(S)-methyl-1-[(S)-N-p-tol uenesulfonylprolyl]-2,3-dihydroindole (Compound (a)) having the following physical characteristics.

It was confirmed that 2-position asymmetric carbon atom of the obtained pyrroloquinoline ring is S-configuration, since it was confirmed by X-ray diffraction that the following compound (b) is R-configuration.

White edged crystals, mp: 168°–170° C.

$[\alpha]_D^{20} = -10.38°$ (c=1.06, chloroform)

Elemental analysis for $C_{21}H_{22}F_2N_2O_3S$: Calcd.: C:59.90, H:5.27, N:6.66; Found: C:59.73, H:5.24, N:6.74.

Figure 1:
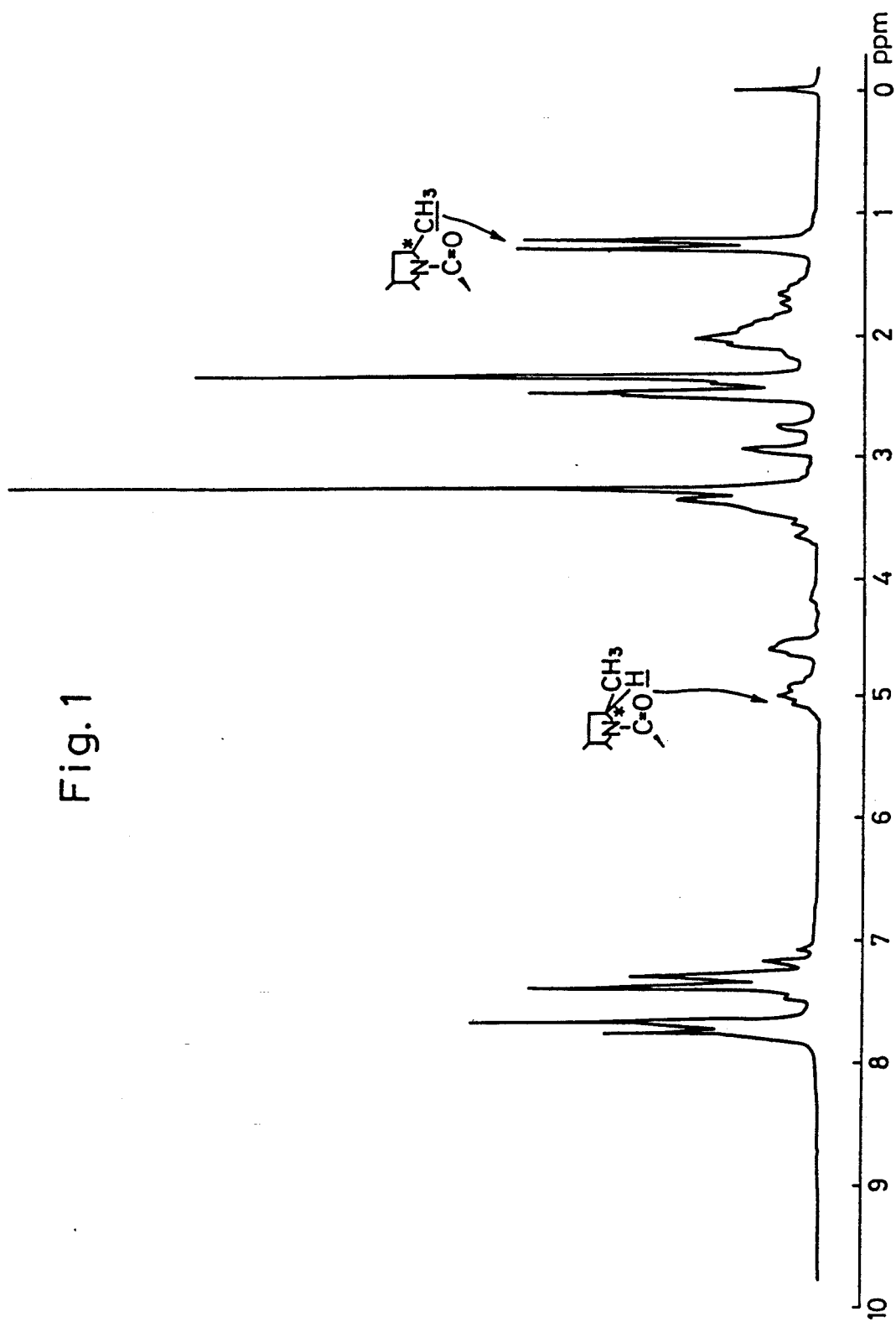
FIG. 1 is the $^1$H-NMR spectrum of the Compound (a)

The NMR spectrum of the Compound a is shown in FIG. 1. The typical peaks are shown below.

$^1$H-NMR (DMSO-d$_6$/TMS) δ: 1.26 (3H, d, J=6.15 HZ), 1.63–2.2 (4H, m), 2.36 (3H, s), 2.8 (1H, d, J=13.5 Hz), 3.2–3.7 (3H, m), 4.5–4.7 (1H, m), 4.8–5.2 (1H, m), 7.3(2H, d, J=8.35 Hz), 7.7 (2H, d, J=8.35 Hz) 7.07–7.5 (1H, m), 7.6–7.9 (1H, m)

When the Compound (a) having the physical characteristics shown above is used as the starting substance, the compounds of this invention in Examples 3, 5, 7–9, and 12–19 which are excellent in their antimicrobial activity can be obtained.

The by-product was recrystallized to give (−)-4,5-difuluoro-2-(R)-methyl-1-[(S)-N-p-toluenesulfonylprolyl]-2,3-dihydroindole (Compound (b)) having the physical characteristics described below.

It was confirmed by X-ray diffraction that 2-position asymmetric carbon atom of the pyrroloquinoline ring is R-configuration.

mp: 236°–239° C.

$[\alpha]_D^{20} = -71.84°$ (c=1.04, chloroform)

Figure 2:
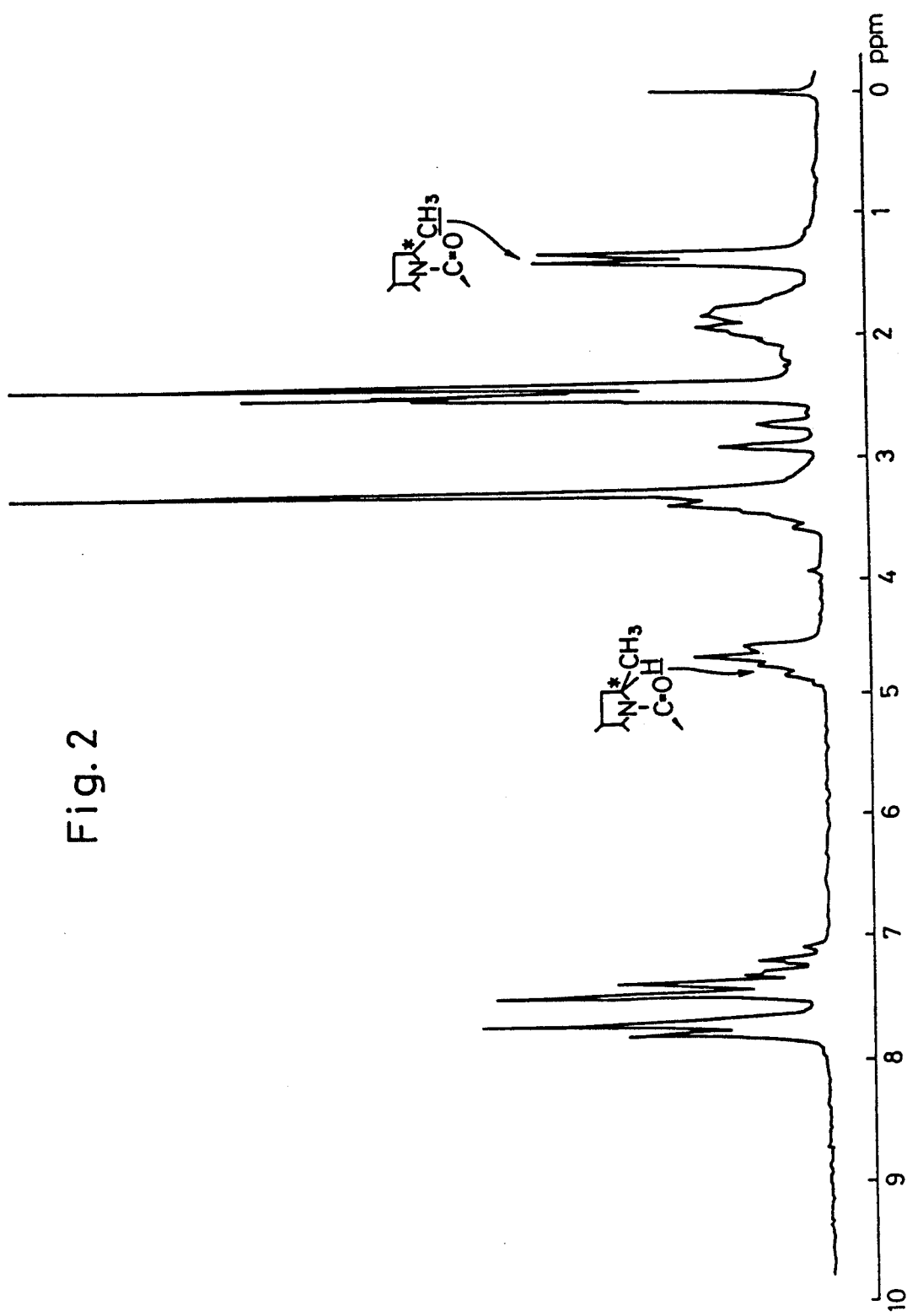
FIG. 2 is the $^1$H-NMR spectrum of the Compound (b).

The NMR spectrum of this compound is shown in FIG. 2. The typical peaks are shown in the following.

$^1$H-NMR (DMSO-d$_6$/TMS) δ: 1.36 (3H, d, J=6.15 HZ), 1.63-2.25 (4H, m), 2.41 (3H, s), 2.83 (1H, d, J=13.5 Hz), 3.05-3.64 (3H, m), 4.5-4.95 (2H, m), 7.41 (2H, d, J=8.35 Hz), 7.74 (2H, d, J=8.35 Hz), 7.07-7.55 (1H, m), 7.6-7.9 (1H, m)

EXAMPLE 2

Synthesis of (+)-4,5-dichloro-2-(S)-methyl-1-[(S)-N-p-toluenesulfonylprolyl]-2,3-dihydroindole (±)-4,5-dichloro-2-methyl-2,3-dihydroindole was used as the starting substance, and the title compound was obtained in a manner analogous to in Example 1.

white edged crystals, mp: 170°-173° C.

[α]$_D^{20}$= +43.0° (c=0.4, chloroform)

Elemental analysis for C$_{21}$H$_{22}$Cl$_2$N$_2$O$_3$S: Calcd.: C:55.63, H:4.86, N:6.18; Found: C:55.46, H:4.78, N:6.14.

EXAMPLE 3

Synthesis of (−)-4,5-difluoro-2-(S)-methyl-2,3-dihydroindole p-toluenesulfonate (−)-4,5-difluoro-2-(S)-methyl-1-[(S)-N-p-toluenesulfonylprolyl]-2,3-dihydroindole, the compound (a) obtained in Example 1, 51.7 g, was added to the solution comprising 69 g of potassium hydroxide, 50 ml of water and 200 ml of methanol, and the mixture was refluxed by heating for 3.5 hours. After the reaction the mixture was allowed to cool to the room temperature, concentrated under reduced pressure to the ¼ volume, to which was added 800 ml of water, and extracted twice with 400 ml of ether. The ether layer was washed with 300 ml of water and a saturated aqueous solution of sodium chloride, and the organic layer was dried over magnesium sulfate and filtered. To the filtrate was added 24 g of p-toluenesulfonic acid monohydrate, and stirred for 30 minutes. The precipitate was collected by filtration, and recrystallized from ethyl acetate-edthanol, to give 25.8 g of the title compound.

white edged crystals mp: 144°-147° C.

[α]$_D^{20}$= −2.22° (C=1.35, methanol)

Elemental analysis for C$_{16}$H$_{17}$F$_2$NO$_3$S: Calcd.: C:56.29, H:5.02, N:4.10; Found: C:56.13, H:5.03, N:4.11.

EXAMPLE 4

Synthesis of (−)-4,5-dichloro-2-(S)-methyl-2,3-dihydroindole

The compound obtained in Example 2 was used as the starting substance, and treated in a manner analogous to Example 3, to give the title compound.

oily substance

[α]$_D^{20}$= −27.6° (c=1.2, chloroform)

EXAMPLE 5

Synthesis of (+)-8,9-difluoro-2-(S)-methyl-6-oxo-1,2-dihydro-6H-pyrrolo[3,2,1-ij]quinoline-5-carboxylic acid To 9 g of (−)-4,5-difluoro-2-(S)-methyl-2,3-dihydroindole obtained in Example 3 was added 11.5 g of diethylethoxymethylene malonate, and heated at 140°-150° C. for 30 minutes. After cooling, to the reaction mixture was added polyphosphoric acid prepared from 32.1 g of phosphoric acid and 32.1 g of phosphorus pentaoxide, and heated at 140°-150° C. for 30 minutes. After the reaction the resultant mixture was cooled to the room temperature, and added to 600 ml of ice-water. The mixture was adjusted to pH 3 with a 20% aqueous solution of sodium hydroxide and the precipitating solid was collected by filtration. The solid was added to a mixture comprising 117 ml of acetic acid and 30 ml of concentrated hydrochloric acid, and refluxed by heating for 5.5 hours. The reaction mixture was added to 1 l of ice-water. The precipitates formed were collected by filtration, washed with water, with isopropanol, and with ether, in this order, and dried, to give 8.86 g of the title compound.

mp: 279°-283° C.

[α]$_D^{20}$= +26.32° (c=0.57, DMSO)

A part of the product was recrystallized from DMF-H$_2$O

Elemental analysis for C$_{13}$H$_9$F$_2$NO$_3$: Calcd.: C:58.87, H:3.42, N:5.28; Found: C:58.87, H:3.15, N:5.28.

EXAMPLE 6

Synthesis of (+)-8,9-dichloro-2-(S)-methyl-6-oxo-1,2-dihydro-6H-pyrrolo[3,2,1-ij]quinoline-5-carboxylic acid The compound obtained in Example 4 was used as the starting substance, and treated in a manner analogous to Example 5, to give the title compound.

mp: 268°-270° C.

[α]$_D^{20}$= +15.5° (c=0.5, 1N-NaOH)

Elemental analysis for C$_{13}$H$_9$Cl$_2$NO$_3$: Calcd.: C:52.35, H:3.02, N:4.70; Found: C:52.24, H:2.98, N:4.91.

EXAMPLE 7

Synthesis of (+)-8-fluoro-2-(S)-methyl-9-(4-methyl-1-piperazinyl)-6-oxo-1,2-dihydro-6H-pyrrolo[3,2,1-ij]quinoline-5-carboxylic acid and the hydrochloride of the same (+)-8.9-difluoro-2-(S)-methyl-6-oxo-1,2-dihydro-6H-pyrrolo[3,2,1-ij]quinoline-5-carboxylic acid obtained in Example 5, 13.5 g, was suspended in 500 ml of diethyl ether, to which was added 70 ml of boron trifluoride-diethyl ether complex, and stirred at room temperature for 5 hours. After the reaction, the precipitates were collected by filtration, washed with diethyl ether, and dried. The precipitates were dissolved in 100 ml of the xamethylphosphoric triamide, to which were added 14.2 ml of triethylamine and 7.5 ml of N-methylpiperazine, and stirred at 40° C. for 10 hours. The solvent was evaporated off under reduced pressure, and to the residue was added diethyl ether. The precipitating yellow solid was collected by filtration. The solid was suspended in 400 ml of methanol, to which was added 25 ml of triethylamine, and refluxed by heating for 25 hours. The solvent was evaporated off under reduced pressure, to the residue was added 300 ml of water, the mixture was adjusted to pH 1 with a 10% aqueous hydrochloric acid, and the insoluble matters were filtered off. The filtrate was concentrated under reduced pressure, and the residue was recrystallized from ethanol-water, to give the hydrochloride of the title compound.

The physical characteristics are described below.

Pale yellow edged crystals, mp: 285°-290° C. (decomposed)

[α]$_D^{20}$= +10.70° (c=0.873, 1N-NaOH)

Elemental analysis for C$_{18}$H$_{20}$FN$_3$O$_3$·HCl·H$_2$O: Calcd.: C:54.07, H:5.79, N:10.51; Found: C:54.31, H:5.63, N:10.62; Ratio of dissolution to water (at 20° C.):230 mg/ml.

The hydrochloride was dissolved in 200 ml of water, and the solution was adjusted to pH 11 with a 20% aqueous NaOH and then to pH 7.3 with a 10% aqueous hydrochloric acid. The resultant solution was extracted three times with 2 l of chloroform, and the organic layer was dried with anhydrous sodium sulfate. Chloroform was evaporated off, and the resultant solid was recrystallized from DMF-ethanol, to give 10.5 g of the title compound.

Pale yellow edged crystals, mp: 250°–253° C.
$[\alpha]_D^{20} = +9.24°$ (c=0.866, DMSO)

Elemental analysis for $C_{18}H_{20}FNO_3$: Calcd.: C:62.60, H:5.84, N:12.17; Found: C:62.40, H:5.85, N:12.13.

EXAMPLE 8

Synthesis of (+)-8-fluoro-2-(S)-methyl-9-(3-methyl-1-piperazinyl)-6-oxo-1,2-dihydro-6H-pyrrolo[3,2,1-ij]quinoline-5-carboxylic acid hydrochloride (+)-8,9-difluoro-2-(S)-methyl-6-oxo-1,2-dihydro-6H-pyrrolo[3,2,1-ij]quinoline-5-carboxylic acid obtained in Example 5, 3 g, was suspended in 30 ml of hexamethylphosphoric triamide, to which was added 3.4 g of 2-methylpiperazine, and allowed to react in an oil bath at 120°–130° C. for 1 hour. The solvent was evaporated off under reduced pressure, to the residue was added ethyl acetate, and the precipitates were collected by filtration. The precipitates were suspended in 150 ml of water, the suspension was adjusted to pH 8 with a 1N sodium hydroxide solution and then to pH 1 with a 10% aqueous hydrochloric acid. The water layer was treated with active carbon and concentrated, and the resultant residue was recrystallized from ethanol-water, to give 3.28 g of the title compound.

Pale yellow edged crystals, mp: 278°–283° C. (decomposed)
$[\alpha]_D^{20} = +27.52°$ (c=0.545, 1N-NaOH)

Elemental analysis for $C_{18}H_{20}FN_3O_3 \cdot HCl \cdot H_2O$: Calcd.: C:54.01, H:5.75, N:10.50; Found: C:54.28, H:5.56, N:10.55.

Ratio of dissolution to water (at 20° C.): 385 mg/ml
$^1$H-NMR (DMSO-$d_6$) δ: 1.30 (d, 3H, J=6 Hz), 1.63 (d, 3H, J=6 Hz), 2.95–4.05 (m, 7H), 4.9–5.3 (d, 1H), 7.64 (d, 1H, J=12 Hz), 8.96 (s, 1H)

In addition, by the alkali-hydrolysis of the above hydrochrolide in accordance with the known method, (+)-8-fluoro-2-(S)-methyl-9-(3-methyl-1-piperazinyl)-6-oxo-1,2-dihydro-6H-pyrrolo[3,2,1-ij]quinoline-5-carboxylic acid was obtained.

$[\alpha]_D^{22} = +25.5°$ (c=1.02, 1N-NaOH)

Ratio of dissolution to water (at 20° C.): 143 mg/ml
$^1$H-NMR (DMSO-$d_6$) δ: 1.31 (d, 3H, J=6 Hz), 1.65 (d, 3H, J=6 Hz), 2.53 (6s, 2H), 2.95–4.1 (m), 4.9–5.3 (2H, m), 7.63 (d, 1H, J=12 Hz), 8.92 (s, 1H)

EXAMPLE 9

Synthesis of (+)-8-fluoro-2-(S)-methyl-9-(3,4-dimethyl-1-piperazinyl)-6-oxo-1,2-dihydro-6H-pyrrolo[3,2,1-ij]quinoline-5-carboxylic acid To 7 g of (+)-8-fluoro-2-(S)-methyl-9-(3-methyl-1-piperazinyl)-6-oxo-1,2-dihydro-6H-pyrrolo[3,2,1-ij]quinoline-5-carboxylic acid obtained in Example 8 were added 36 g of sodium formate, 90 ml of 99% formic acid, and 90 ml of 37% formalin, and refluxed by heating for 3 hours. After the reaction the mixture was concentrated under reduced pressure, to the residue was added 200 ml of water, and the mixture was adjusted to pH 7.5 with a 20% aqueous sodium hydroxide. The mixture was extracted twice with 500 ml of chloroform, and the organic layer was washed with a saturated solution of sodium chloride and then with water, and dried with anhydrous sodium sulfate.

Chloroform was evaporated off, and the residue was recrystallized from benzene-n-hexane to give 5.5 g of the title compound.

Pale yellow edged crystals, mp: 210°–212° C. (decomposed) $[\alpha]_D^{20} = +10.53°$ (c=0.57, 1N-NaOH)

Elemental analysis for $C_{19}H_{22}FN_3O_3$: Calcd.: C:63.50, H:6.17, N:11.69; Found: C:63.20, H:6.17, N:11.55.

By treating this compound with 10% aqueous hydrochloric acid, (+)-8-fluoro-2-(S)-methyl-9-(3,4-dimethyl-1-piperazinyl)-6-oxo-1,2-dihydro-6H-pyrrolo[3,2,1-ij]quinoline-5-carboxylic acid hydrochloride was obtained.

Pale yellow edged crystals, mp: 278°–282° C. (decomposed)
$[\alpha]_D^{20} = +12.13°$ (c=0.58, 1N-NaOH)

Elemental analysis for $C_{19}H_{22}FN_3O_3 \cdot H_2O \cdot HCl$: Calcd.: C:55.14, H:6.09, N:10.15; Found: C:55.29, H:5.97, N:10.34.

EXAMPLE 10

(±)-8-fluoro-2-methyl-9-(3-methyl-1-piperazinyl)-6-oxo-1,2-dihydro-6H-pyrrolo[3,2,1-ij]quinoline-5-carboxylic acid hydrochloride (±)-8,9-difluoro-2-methyl-6-oxo-1,2-dihydro-6H-pyrrolo[3,2,1-ij]quinoline-5-carboxylic acid was used as the starting substance, and treated in a manner analogous to Example 8, to give the title compound.

Pale yellow edged crystals, mp: 258°–261° C. (decomposed)

Elemental analysis for $C_{18}H_{20}FN_3O_3 \cdot HCl \cdot H_2O$: Calcd.: C:54.01, H:5.75, N:10.50; Found: C:53.86, H:5.82, N:10.36.

Ratio of dissolution to water (at 20° C.): 152 mg/ml

EXAMPLE 11

Synthesis of (+)-8-chloro-2-(S)-methyl-9-(3-methyl-1-piperazinyl)-6-oxo-1,2-dihydro-6H-pyrrolo[3,2,1-ij]quinoline-5-carboxylic acid hydrochloride (+)-8,9-dichloro-2-(S)-methyl-6-oxo-1,2-dihydro-6H-pyrrolo[3,2,1-ij]quinoline-5-carboxylic acid obtained in Example 6 and 2-methylpiperazine were used as the starting substances, and treated in a manner analogous to Example 8, to give the title compound.

Pale yellow edged crystals, mp: 268°–270° C. (decomposed)
$[\alpha]_D^{20} = +15.5°$ (c=0.50, 1N-NaOH)

Elemental analysis for $C_{18}H_{20}ClN_3O_3 \cdot HCl \cdot H_2O$: Calcd.: C:51.92, H:5.53, N:10.10; Found: C:51.69, H:5.42, N:9.92.

Ratio of dissolution to water (at 20° C.): 231 mg/ml

EXAMPLE 12

Synthesis of (+)-8-fluoro-2-(S)-methyl-9-(3,5-dimethyl-1-piperazinyl)-6-oxo-1,2-dihydro-6H-pyrrolo[3,2,1-ij]quinoline-5-carboxylic acid hydrochloride The compound obtained in Example 5 and 2,6-dimethylpiperazine were used as the starting substances, and treated in a manner analogous to Example 8, give the title compound.

Pale yellow edged crystals, mp: 288°–295° C. (decomposed)
$[\alpha]_D^{20} = +10.59°$ (c=0.85, 1N-NaOH)

Elemental analysis for $C_{19}H_{23}ClFN_3O_3 \cdot 2H_2O$: Calcd.: C:52.84, H:6.30, N:9.73; Found: C:52.56, H:5.98, N:9.47.

Ratio of dissolution to water (at 20° C.): 175 mg/ml

EXAMPLE 13

Synthesis of (+)-8-fluoro-2-(S)-methyl-9-(3,4,5-trimethyl-1-piperazinyl)-6-oxo-1,2-dihydro-6H-pyrrolo[3,2,1-ij]quinoline-5-carboxylic acid The compound obtained in Example 5 and 1,2,6-trimethylpiperazine were used, and treated in a manner analogous to Example 9, to give the title compound.

Pale yellow edged crystals, mp: 204°–206° C.

$[\alpha]_D^{20} = +16.57°$ (c=0.905, 1N-NaOH)

Elemental analysis for $C_{20}H_{24}FN_3O_3$: Calcd.: C:64.33, H:6.48, N:11.25; Found: C:64.11, H:6.24, N:11.06.

And (+)-8-fluoro-2-(S)-methyl-9-(3,4,5-trimethyl-1-piperazinyl)-6-oxo-1,2-dihydro-6H-pyrrolo[3,2,1-ij]quinoline-5-carboxylic acid hydrochoride was obtained by treating with 10% aqueous hydrochloric acid.

Pale yellow sharp-edged crystals, mp: 268°–271° C. (decomposed)

$[\alpha]_D^{20} = +18.99°$ (c=0.913, 1N-NaOH)

Elemental analysis for $C_{20}H_{24}FN_3O_3 \cdot HCl \cdot H_2O$: Calcd.: C:56.14, H:6.36, N:9.82; Found: C:55.88, H:6.45, N:9.71.

EXAMPLE 14

Synthesis of (−)-8-fluoro-2-(S)-methyl-9-(3-S-methyl-1-piperazinyl)-6-oxo-1,2-dihydro-6H-pyrrolo[3,2,1-ij]quinoline-5-carboxylic acid hydrochloride (+)-8,9-difluoro-2-(S)-methyl-6-oxo-1,2-dihydro-6H-pyrrolo[3,2,1-ij]quinoline-5-carboxylic acid obtained in Example 5 and (S)-(+)-2-methylpiperazine were used, and treated in a manner analogous to Example 8, to give the title compound.

Pale yellow edged crystals, mp: 299° C. (decomposed)

$[\alpha]_D^{20} = -1.67°$ (c=0.60, 1N-NaOH)

Elemental analysis for $C_{18}H_{20}FN_3O_3 \cdot HCl \cdot H_2O$: Calcd.: C:54.01, H:5.75, N:10.50; Found: C:53.92, H:5.93, N:10.24.

EXAMPLE 15

Synthesis of (+)-8-fluoro-2-(S)-methyl-9-((3S)-3,4-dimethyl-1-piperazinyl)-6-oxo-1,2-dihydro-6H-pyrrolo[3,2,1-ij]quinoline-5-carboxylic acid (−)-8-fluoro-2-(S)-methyl-9-(3-(S)-methyl-1-piperazinyl)-6-oxo-1,2-dihydro-6H-pyrrolo[3,2,1-ij]quinoline-5-carboxylic acid obtained in Example 14 was used, and treated in a manner analogous to Example 9, to give the title compound.

Pale yellow edged crystals mp: 217°–219° C.

$[\alpha]_D^{20} = +2.86°$ (c=0.35, 1N-NaOH)

Elemental analysis for $C_{19}H_{22}FN_3O_3$: Calcd.: C:63.50, H:6.17, N:11.69; Found: C:63.63, H:6.05, N:11.47.

By treating this with 10% aqueous hydrochloric acid (+)-8-fluoro-2-(S)-methyl-9-((3S)-3,4-dimethyl-1-piperazinyl)-6-oxo-1,2-dihydro-6H-pyrrolo[3,2,1-ij]-quinoline-5-carboxylic acid hydrochloride was obtained.

Pale yellow edged crystals, mp: 281°–283° C. (decomposed)

$[\alpha]_D^{20} = +3.30°$ (c=0.36, 1N-NaOH)

Elemental analysis for $C_{19}H_{22}FN_3O_3 \cdot HCl \cdot H_2O$: Calcd.: C:55.14, H:6.09, N:10.15; Found: C:54.97, H:6.22, N:10.03.

EXAMPLE 16

Synthesis of (+)-8-fluoro-2-(S)-methyl-9-(3-(R)-methyl-1-piperazinyl)-6-oxo-1,2-dihydro-6H-pyrrolo[3,2,1-ij]quinoline-5-carboxylic acid hydrochloride (+)-8,9-difluoro-2-(S)-methyl-6-oxo-1,2-dihydro-6H-pyrrolo [3,2,1-ij]quinoline-5-carboxylic acid obtained in Example 5 and (R)-(−)-2-methylpiperazine were used, and treated in a manner analogous to Example 8, to give the title compound.

Pale yellow edged crystals, mp: 295° C. (decomposed)

$[\alpha]_D^{20} = +35.29°$ (c=0.68, 1N-NaOH)

Elemental analysis for $C_{18}H_{20}FN_3O_3 \cdot HCl \cdot H_2O$: Calcd.: C:54.01, H:5.75, N:10.50; Found: C:54.17, H:5.82, N:10.38.

EXAMPLE 17

Synthesis of (+)-8-fluoro-2-(S)-methyl-9-(3-amino-1-pyrrolidyl)-6-oxo-1,2-dihydro-6H-pyrrolo[3,2,1-ij]quinoline-5-carboxylic acid To 7 g of (+)-8,9-difluoro-2-(S)-methyl-6-oxo-1,2-dihydro-6H-pyrrolo[3,2,1-ij]quinoline-5-carboxylic acid obtained in Example 5 were added 21 g of aminopyrrolidine dihydrochloride, 40 ml of 1,8-diazabicyclo[5,4,0]-7-undecene (DBU) and 70 ml of hexamethylphosphoric triamide, and allowed to react in an oil bath at 120°–130° C. for 2 hours. The solvent was evaporated off under reduced pressure, and the residue was dissolved in 100 ml of 2% aqueous hydrochloric acid. Insoluble matters were filtered off, the filtrate was concentrated, and the residue was recrystallized from ethanol-water to obtain (+)-8-fluoro-2-methyl-9-(3-amino-1-pyrrolidyl)-6-oxo-1,2-dihydro-6H-pyrrolo[3,2,1-ij]quinoline-5-carboxylic acid hydrochloride.

Pale green-yellow edged crystals, mp: 258°–262° C. (decomposed)

$[\alpha]_D^{20} = +125.1°$ (c=0.34, 1N-NaOH)

Elemental analysis for $C_{17}H_{18}FN_3O_3 \cdot HCl \cdot 2H_2O$: Calcd.: C:50.56, H:5.74, N:10.41; Found: C:50.33, H:5.57, N:10.27.

Ratio of dissolution to water (at 20° C.): 158 mg/ml

The crystals obtained were dissolved in 30 ml of water, and the solution was adjusted to pH 8 by adding a saturated solution of sodium hydrogencarbonate. The resulting crystals were collected by filtration, and dried to give 1.4 g of the title compound.

Pale green edged crystals, mp: 265°–271° C. (decomposed)

$[\alpha]_D^{20} = +119.4°$ (c=0.335, 1N-NaOH)

Elemental analysis for $C_{17}H_{18}FN_3O_3 \cdot 3H_2O$: Calcd.: C:52.98, H:6.28, N:10.90; Found: C:53.03, H:6.04, N:10.80.

EXAMPLE 18

Synthesis of (+)-8-fluoro-2-(S)-methyl-9-[3-(ethylaminomethyl)-1-pyrrolidinyl]-6-oxo-1,2-dihydro-6H-pyrrolo[3,2,1-ij]quinoline-5-carboxylic acid hydrochloride (+)-8,9-difluoro-2-(S)-methyl-6-oxo-1,2-dihydro-6H-pyrrolo[3,2,1-ij]quinoline-5-carboxylic acid obtained in Example 5 and 3-(ethylaminomethyl)-pyrrolidine were used, and treated in a manner analogous to Example 8, to give the title compound.

Pale yellow edged crystals mp: 263°–265° C. (decomposed)

$[\alpha]_D^{20} = +42.51°$ (c=0.82, 1N-NaOH)

Elemental analysis for $C_{20}H_{24}FN_3O_3 \cdot HCl \cdot H_2O$: Calcd.: C:56.14, H:6.32, N:9.82; Found: C:55.81, H:6.08, N:10.19.

Ratio of dissolution to water (at 20° C.): 195 mg/ml

EXAMPLE 19

Synthesis of (+)-8-fluoro-2-(S)-methyl-9-[3-(isopropylaminomethyl)-1-pyrrolidyl]-6-oxo-1,2-dihydro-6H-pyrrolo[3,2,1-ij]quinoline-5-carboxylic acid hydrochloride (+)-8,9-difluoro-2-(S)-methyl-6-oxo-1,2-dihydro-6H-pyrrolo[3,2,1-ij]quinoline-5-carboxylic acid obtained in Example 5 and 3-(isopropylaminomethyl)-pyrrolidine were used, and treated in a manner analogous to Example 8, to give the title compound.

Pale yellow edged crystals mp: 237°–241° C. (decomposed)

$[\alpha]_D^{20} = +17.36°$ (c=0.76, 1N-NaOH)

Elemental analysis for $C_{21}H_{26}FN_3O_3 \cdot HCl \cdot 2H_2O$: Calcd.: C:54.84, H:6.75, N:9.14; Found: C:54.50, H:6.52, N:9.06.

Ratio of dissolution to water (at 20° C.): 135 mg/ml

EXAMPLE 20

Synthesis of (+)-8-fluoro-2-(S)-methyl-9-(3-methyl-1-piperazinyl)-6-oxo-1,2-dihydro-6H-pyrrolo[3,2,1-ij]quinoline-5-carboxylic acid To 1 g of (+)-8-fluoro-2-(S)-methyl-9-(3-methyl-1-piperazinyl)-6-oxo-1,2-dihydro-6H-pyrrolo[3,2,1-ij]quinoline-5-carboxylic acid hydrochloride obtained in Example 8 was dissolved in 20 ml of water, and to which was added 5 g of Bio-Red AG3-X4(OH form) [manufactured by Bio-Red Laboratories]. The reaction was conducted for 10 minutes at room temperature. After the reaction, resin was filtered off and the filtrat was concentrated under reduced pressure. To the residue was added 10 ml of ethanol, to give powder matters.

The residue was filtered and washed with ethanol and n-hexane, to give 0.69 g of the title compound.

Pale yellow amorphism, mp: over 290° C. changing to black $[\alpha]_D^{22} = +25.5°$ (c=1.02, 1N-NaOH)

$^1$H-NMR (DMSO-d$_6$) δ:1.30 (d, 3H, J=6 Hz), 1.63 (d, 3H, J=6 Hz), 2.95–4.05 (m, 7H), 4.9–5.3 (m, 1H), 7.64 (d, 1H, J=12 Hz), 8.96 (s, 1H)

EXAMPLE 21

Synthesis of (+)-8-fluoro-2-(S)-methyl-9-(3-methyl-1-piperazinyl)-6-oxo-1,2-dihydro-6H-pyrrolo[3,2,1-ij]quinoline-5-carboxylic acid ½-sulfate To 0.5 g of (+)-8-fluoro-2-(S)-methyl-9-(3-methyl-1-piperazinyl)-6-oxo-1,2-dihydro-6H-pyrrolo[3,2,1-ij]quinoline-5-carboxylic acid obtained in Example 20 was dissolved in 10 ml of water, and was adjusted to pH 1 with 1N-sulfulic acid. The water layer was concentrated under reduced pressure, and the residue obtained was recrystallized from ethanol-water, to give 0.41 g of the title compound.

White edged crystals, mp: 262°–265° C. (decomposed)

$[\alpha]_D^{20} = +27.15°$ (c=0.551, 1N-NaOH)

Elemental analysis for $C_{18}H_{20}FN_3O_3 \cdot HCl \cdot ½H_2SO_4$: Calcd.: C:54.82, H:5.37, N:10.65; Found: C:54.66, H:5.31, N:10.53.

EXAMPLE 22

Synthesis of (+)-8-fluoro-2-(S)-methyl-9-(3-methyl-1-piperazinyl)-6-oxo-1,2-dihydro-6H-pyrrolo[3,2,1-ij]quinoline-5-carboxylic acid methanesulfonate (+)-8-fluoro-2-(S)-methyl-9-(3-methyl-1-piperazinyl)-6-oxo-1,2-dihydro-6H-pyrrolo[3,2,1-ij]quinoline-5-carboxylic acid and methanesulfonic acid were used, and treated in a manner analogous to Example 21, to give the title compound.

Pale yellow edged crystals, mp: 247°–251° C. (decomposed)

$[\alpha]_D^{20} = +31.62°$ (c=0.554, 1N-NaOH)

Elemental analysis for $C_{18}H_{20}FN_3O_3 \cdot CH_3 \cdot SO_3H \cdot H_2O$: Calcd.: C:49.66, H:5.70, N:9.14; Found: C:49.80, H:5.64, N:9.08.

REFERENCE EXAMPLE 1

Synthesis of (−)-8-fluoro-2-(R)-methyl-9-(4-methyl-1-piperazinyl)-6-oxo-1,2-dihydro-6H-pyrrolo[3,2,1-ij]quinoline-5-carboxylic acid (−)-8,9-difluoro-2-(R)-methyl-6-oxo-1,2-dihydro-6H-pyrrolo[3,2,1-ij]quinoline-5-carboxylic acid (Compound (b)) and N-methylpiperazine were used, and treated in a manner analogous to Example 7, to give the title compound.

Pale yellow edged crystals, mp: 249°–252° C.

$[\alpha]_D^{20} = -8.98°$ (c=0.806, DMSO)

The corresponding hydrochloride was prepared from the above compound by the conventional method. Ratio of dissolution to water (at 20° C.): 12 mg/ml

REFERENCE EXAMPLE 2

Synthesis of (−)-8-fluoro-2-(R)-methyl-9-(3-methyl-1-piperazinyl)-6-oxo-1,2-dihydro-6H-pyrrolo[3,2,1-ij]quinoline-5-carboxylic acid hydrochloride (−)-8,9-difluoro-2-(R)-methyl-6-oxo-1,2-dihydro-6H-pyrrolo[3,2,1-ij]quinoline-5-carboxylic acid and N-methylpiperazine were used, and treated in a manner analogous to Example 8, to give the title compound.

$[\alpha]_D^{20} = -18.00°$ (c=1.00, 1N-NaOH)

Ratio of dissolution to water (at 20° C.): 167 mg/ml $^1$H-NMR (DMSO-d$_6$) δ: 1.30 (d, 3H, J=6 Hz), 1.63 (d, 3H, J=6 Hz), 2.95–4.05 (m, 7H), 4.9–5.3 (m, 1H), 7.64 (d, 1H, J=12 Hz), 8.96 (s, 1H)

PHARMACOLOGICAL ACTIVITY TEST
EXAMPLE 1

In order to investigate the in vitro activity of the under-mentioned compounds against various bacteria, the minimal inhibitory concentration (MIC, μ g/ml) values were determined by the agar plate dilution method [see Chemotherapy, 22, 1126–1128 (1974)].

The results are shown in Table 1.

TEST COMPOUND A (+)-8-fluoro-2-(S)-methyl-9-(4-methyl-1-piperazinyl)-6-oxo-1,2-dihydro-6H-pyrrolo[3,2,1-ij]quinoline-5-carboxylic acid (a compound according to the present invention, Example 7)

TEST COMPOUND B (+)-8-fluoro-2-(S)-methyl-9-(3-methyl-1-piperazinyl)-6-oxo-1,2-dihydro-6H-pyrrolo[3,2,1-ij]quinoline-5-carboxylic acid hydrochloride (a compound according to the present invention, Example 8)

TEST COMPOUND C (+)-8-fluoro-2-(S)-methyl-9-(3,4-dimethyl-1-piperazinyl)-6-oxo-1,2-dihydro-6H-pyrrolo[3,2,1-ij]quinoline-5-carboxylic acid (a compound according to the present invention, Example 9)

TEST COMPOUND D (±)-8-fluoro-2-methyl-9-(3-methyl-1-piperazinyl)-6-oxo-1,2-dihydro-6H-pyrrolo[3,2,1-ij]quinoline-5-carboxylic acid hydrochloride (a compound according to the present invention, Example 10)

TEST COMPOUND E (+)-8-chloro-2-(S)-methyl-9-(3-methyl-1-piperazinyl)-6-oxo-1,2-dihydro-6H-pyrrolo[3,2,1-ij]quinoline-5-carboxylic acid . hydrochloride (a compound according to the present invention, Example 11)

TEST COMPOUND F (+)-8-fluoro-2-(S)-methyl-9-(3,5-dimethyl-1-piperazinyl)-6-oxo-1,2-dihydro-6H-pyrrolo[3,2,1-ij]quinoline-5-carboxylic acid . hydrochloride (a compound according to the present invention, Example 12)

TEST COMPOUND G (+)-8-fluoro-2-(S)-methyl-9-(3,4,5-trimethyl-1-piperazinyl)-6-oxo-1,2-dihydro-6H-pyrrolo[3,2,1-ij]quinoline-5-carboxylic acid (a compound according to the present invention, Example 13)

TEST COMPOUND H (−)-8-fluoro-2-(S)-methyl-9-(3-S-methyl-1-piperazinyl)-6-oxo-1,2-dihydro-6H-pyrrolo[3,2,1-ij]quinoline-5-carboxylic acid . hydrochloride (a compound according to the present invention, Example 14)

TEST COMPOUND I (+)-8-fluoro-2-(S)-methyl-9-((3S)-3,4-dimethyl-1-piperazinyl)-6-oxo-1,2-dihydro-6H-pyrrolo[3,2,1-ij]quinoline-5-carboxylic acid (a compound according to the present invention, Example 15)

TEST COMPOUND J (+)-8-fluoro-2-(S)-methyl-9-(3-(R)-methyl-1-piperazinyl)-6-oxo-1,2-dihydro-6H-pyrrolo[3,2,1-ij]quinoline-5-carboxylic acid . hydrochloride (a compound according to the present invention, Example 16)

TEST COMPOUND K (+)-8-fluoro-2-(S)-methyl-9-(3-amino-1-pyrrolidinyl)-6-oxo-1,2-dihydro-6H-pyrrolo[3,2,1-ij]quinoline-5-carboxylic acid (a compound according to the present invention, Example 17)

TEST COMPOUND L (+)-8-fluoro-2-(S)-methyl-9-[3-(ethylaminomethyl)-1-pyrrolidinyl]-6-oxo-1,2-dihydro-6H-pyrrolo[3,2,1-ij]quinoline-5-carboxylic acid . hydrochloride (a compound according to the present invention, Example 18)

TEST COMPOUND M (+)-8-fluoro-2-(S)-methyl-9-[3-(isopropylaminomethyl)-1-pyrrolidinyl]-6-oxo-1,2-dihydro-6H-pyrrolo[3,2,1-ij]quinoline-5-carboxylic acid . hydrochloride (a compound according to the present invention, Example 19)

TEST COMPOUND N (−)-8-fluoro-2-(R)-methyl-9-(4-methyl-1-piperazinyl)-6-oxo-1,2-dihydro-6H-pyrrolo[3,2,1-ij]quinoline-5-carboxylic acid (Reference Example 1)

TEST COMPOUND O 8-fluoro-2-methyl-9-(4-methyl-1-piperazinyl)-6-oxo-1,2-dihydro-6H-pyrrolo[3,2,1-ij]quinoline-5-carboxylic acid (racemic body, a reference compound, U.S. Pat. No. 4,416,884)

TEST COMPOUND P

S-(−)-9-fluoro-3-methyl-10-(4-methyl-1-piperazinyl)-7-oxo-2,3-dihydro-7H-pyrido[1,2,3-de][1,4]benzoxazine-6-carboxylic acid (ofloxacine, a comparative compound)

TABLE 1

| Strain | (MIC, μg/ml) | | | | | |
|---|---|---|---|---|---|---|
| | Test compound A | Test compound B | Test compound C | Test compound D | Test compound E | Test compound F |
| S. aureus FDA209P | 0.1 | 0.2 | 0.2 | 0.39 | 0.39 | 0.39 |
| E. facalis ATCC-21212 | 0.78 | 3.13 | 1.56 | 6.25 | 6.25 | 6.25 |
| E. coli NIHJ JC-2 | 0.05 | 0.05 | 0.05 | 0.1 | 0.1 | 0.1 |
| K. pneumoniae NCTC-9632 | 0.05 | 0.05 | 0.1 | 0.1 | 0.1 | 0.1 |
| S. marcescens IFO-12648 | 0.05 | 0.1 | 0.2 | 0.2 | 0.2 | 0.2 |
| P. mirabilis ATCC-29906 | 0.2 | 0.1 | 0.39 | 0.2 | 0.2 | 0.39 |
| M. morganii IID Kono | 0.05 | 0.012 | 0.2 | 0.05 | 0.024 | 0.1 |
| P. aeruginosa ATCC-10145 | 1.56 | 0.39 | 3.13 | 0.78 | 0.78 | 3.13 |
| P. aeruginosa E-2 | 0.78 | 0.39 | 1.56 | 0.78 | 0.78 | 3.135 |
| A. calcoaceticus Ac-54 | 0.1 | 0.39 | 0.2 | 0.78 | 0.78 | 0.78 |

| Strain | (MIC, μg/ml) | | | | | |
|---|---|---|---|---|---|---|
| | Test compound G | Test compound H | Test compound I | Test compound J | Test compound K | Test compound L |
| S. aureus FDA209P | 0.2 | 0.2 | 0.1 | 0.2 | 0.2 | 0.2 |
| E. facalis ATCC-21212 | 1.56 | 3.13 | 1.56 | 3.13 | 3.13 | 0.78 |
| E. coli NIHJ JC-2 | 0.05 | 0.024 | 0.05 | 0.05 | 0.05 | 0.2 |
| K. pneumoniae NCTC-9632 | 0.1 | 0.024 | 0.024 | 0.024 | 0.05 | 0.39 |
| S. marcescens IFO-12648 | 0.2 | 0.1 | 0.1 | 0.2 | 0.1 | 0.78 |
| P. mirabilis ATCC-29906 | 0.39 | 0.1 | 0.2 | 0.1 | 0.1 | 0.78 |
| M. morganii IID Kono | 0.2 | 0.012 | 0.1 | 0.024 | 0.024 | 0.78 |
| P. aeruginosa ATCC-10145 | 3.13 | 0.39 | 1.56 | 0.78 | 0.39 | 6.25 |
| P. aeruginosa E-2 | 1.56 | 0.39 | 1.56 | 0.78 | 0.39 | 6.25 |

TABLE 1-continued

| | | | | | | |
|---|---|---|---|---|---|---|
| A. calcoaceticus Ac-54 | 0.2 | 0.39 | 0.2 | 0.78 | 0.39 | 6.25 |

| | (MIC, μg/ml) | | | |
|---|---|---|---|---|
| Strain | Test compound M | Test compound N | Test compound O | Test compound P |
| S. aureus FDA209P | 0.2 | 3.13 | 0.2 | 0.2 |
| E. facalis ATCC-21212 | 0.78 | 100 | 1.56 | 3.13 |
| E. coli NIHJ JC-2 | 0.39 | 0.78 | 0.1 | 0.1 |
| K. pneumoniae NCTC-9632 | 0.39 | 0.78 | 0.1 | 0.1 |
| S. marcescens IFO-12648 | 0.78 | 0.78 | 0.1 | 0.2 |
| P. mirabilis ATCC-29906 | 0.78 | 3.13 | 0.39 | 0.39 |
| M. morganii IID Kono | 0.78 | 0.78 | 0.1 | 0.1 |
| P. aeruginosa ATCC-10145 | 12.5 | 25 | 3.13 | 3.13 |
| P. aeruginosa E-2 | 6.25 | 12.5 | 1.56 | 1.56 |
| A. calcoaceticus Ac-54 | 6.25 | 3.13 | 0.2 | 0.39 |

PHARMACEUTICAL EXAMPLE 1

| | |
|---|---|
| Compound of Example 7 | 2 g |
| Purified lanolin | 5 g |
| White beeswax | 5 g |
| white petrolatum | 88 g |
| Total | 100 g |

White beeswax was melted by warming and, then, the compound according to the present invention, purified lanolin and white petrolatum were added. The mixture was warmed until it formed a liquid and, then stirred until it was solidified to give an ointment of the above composition.

PHARMACEUTICAL EXAMPLE 2

| | |
|---|---|
| Compound of Example 8 | 200 mg |
| Glucose | 250 mg |
| Distilled water for injection | q.s. |

In distilled water for injection were dissolved the compound of the present invention and glucose and the solution was filled into a 5 ml ampul. After nitrogen purging, sterilization was carried out by autoclaving at 121° C. for 15 minutes to give a parenteral product of the above composition.

PHARMACEUTICAL EXAMPLE 3

| | |
|---|---|
| Compound of Example 11 | 100 g |
| Avicel [trademark of Asahi Chemical Industry] | 40 g |
| Corn starch | 30 g |
| Magnesium stearate | 2 g |
| TC-5 [trademark of Shinetsu Chemical: hydroxypropylmethylcellulose] | 10 g |
| Macrogol-6000 | 3 g |
| Castor oil | 40 g |
| Methanol | 40 g |

The compound according to the present invention, avicel, corn starch and magnesium stearate were milled together and tableted by means of R 10 mm punch (for sugar-coated tablets). The resulting tablets were coated with a film coating composition consisting of TC-5, polyethylene glycol (macrogol-6000), castor oil and methanol to give film-coated tablets of the above composition.

What is claimed is:

1. A pyrroloquinoline compound or salt thereof having the formula:

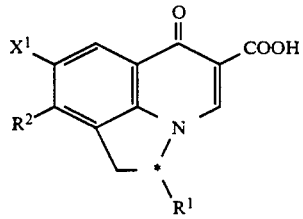

wherein $R^1$ is a $C_1$-$C_6$ alkyl group; $R^2$ is a group:

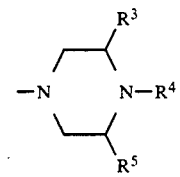

or a group:

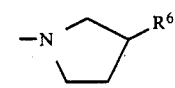

wherein $R^3$, $R^4$ and $R^5$ are the same or different, a hydrogen atom or a $C_1$-$C_6$ alkyl group, and $R^6$ is an amino group or a $C_1$-$C_6$ alkylamino-$C_1$-$C_6$ alkyl group, $X^1$ is a halogen atom and * denotes an asymmetric atom, wherein said asymmetric carbon atom of pyrroloquinoline ring has S-configuration.

2. A pyrroloquinoline compound or salt thereof having the formula:

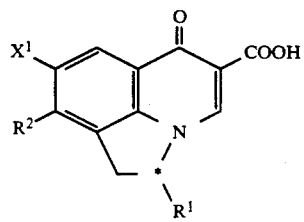

wherein $R^1$ is a $C_1$-$C_6$ alkyl group; $R^2$ is a group:

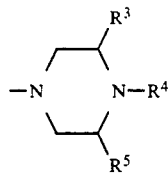

or a group:

wherein $R^3$, $R^4$ and $R^5$ are the same or different, a hydrogen atom or a $C_1$-$C_6$ alkyl group, and $R^6$ is an amino group or a $C_1$-$C_6$ alkylamino-$C_1$-$C_6$ alkyl group, $X^1$ is a halogen atom and * denotes an asymmetric atom, wherein said asymmetric carbon atom of pyrroloquinoline ring has R-configuration.

3. A pyrroloquinoline compound or salt thereof according to claim 1, wherein $R^2$ is a group:

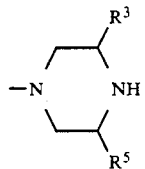

wherein $R^3$ and $R^5$ are the same or different, a hydrogen atom or a $C_1$-$C_6$ alkyl group.

4. A pyrroloquinoline compound or salt thereof according to claim 1, wherein $R^2$ is a group:

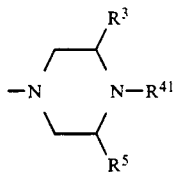

wherein $R^3$ and $R^5$ are the same or different, a hydrogen atom or a $C_1$-$C_6$ alkyl group, and $R^{41}$ is a $C_1$-$C_6$ alkyl group.

5. A pyrroloquinoline compound or salt thereof according to claim 1, wherein $R^2$ is a group:

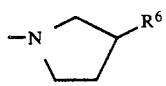

wherein $R^6$ is an amino group or a $C_1$-$C_6$ alkylamino-$C_1$-$C_6$ alkyl group.

6. A pyrroloquinoline compound or salt thereof according to claim 3, wherein alkyl group is methyl group or ethyl group, and $X^1$ is a fluorine atom or a chlorine atom.

7. A pyrroloquinoline compound or salt thereof according to claim 6, wherein $X^1$ is a fluorine atom.

8. A pyrroloquinoline compound or salt thereof according to claim 6, wherein alkyl group is methyl group, and $X^1$ is a chlorine atom.

9. A pyrroloquinoline compound or salt thereof according to claim 7, wherein alkyl group is methyl group.

10. A pyrroloquinoline salt according to claim 9.

11. A pyrroloquinoline compound according to claim 9.

12. A pyrroloquinoline salt according to claim 8.

13. A pyrroloquinoline compound according to claim 8.

14. A pyrroloquinoline salt according to claim 4.

15. A pyrroloquinoline compound according to claim 4.

16. A pyrroloquinoline salt thereof according to claim 14, wherein alkyl group is methyl group, and $X^1$ is a fluorine atom.

17. A pyrroloquinoline compound thereof according to claim 15, wherein alkyl group is methyl group, and $X^1$ is a fluorine atom.

18. A pyrroloquinoline salt thereof according to claim 16, wherein one of $R^3$ and $R^5$ is a hydrogen atom.

19. A pyrroloquinoline salt thereof according to claim 16, wherein $R^3$ and $R^5$ are $C_1$-$C_6$ alkyl groups.

20. A pyrroloquinoline compound or salt thereof according to claim 5, wherein $R^1$ is methyl group, and $X^1$ is a fluorine atom.

21. A pyrroloquinoline salt according to claim 20.

22. A pyrroloquinoline compound according to claim 20.

23. A racemic pyrroloquinoline compound or salt thereof having the formula:

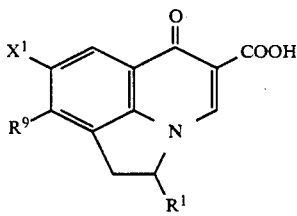

wherein $X^1$ is a fluorine atom, $R^1$ is a methyl group, and $R^9$ is a group:

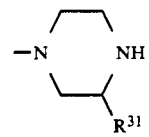

wherein $R^{31}$ is a methyl group or an ethyl group;

24. A racemic pyrroloquinoline compound or salt thereof having the formula:

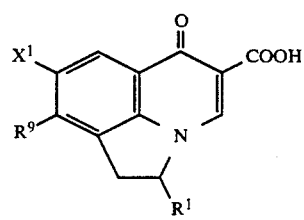

wherein $X^1$ is a fluorine atom, $R^1$ is methyl group, and $R^9$ is a group:

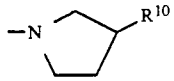

wherein $R^{10}$ is a $C_1$–$C_6$ alkylamino-$C_1$–$C_6$ group.

25. The compound of claim 3 selected from the group consisting of (+)-8-fluoro-2-(S)-methyl-9-(3-methyl-1-piperazinyl)-6-oxo-1,2-dihydro-6H-pyrrolo[3,2,1-ij]quinoline-5-carboxylic acid hydrochloride.

(+)-8-chloro-2-(S)-methyl-9-(3-methyl-1-piperazinyl)-6-oxo-1,2-dihydro-6H-pyrrolo[3,2,1-ij]quinoline-5-carboxylic acid hydrochloride, (+)-8-fluoro-2-(S)-methyl-9-(3,5-dimethyl-1-piperazinyl)-6-oxo-1,2-dihydro-6H-pyrrolo[3,2,1-ij]quinoline-5-carboxylic acid hydrochloride, (−)-8-fluoro-2-(S)-methyl-9-(3-(S)-methyl-1-piperazinyl)-6-oxo-1,2-dihydro-6H-pyrrolo[3,2,1-ij]quinoline-5-carboxylic acid hydrochloride and (+)-8-fluoro-2-(S)-methyl-9-(3-(R)-methyl-1-piperazinyl)-6-oxo-1,2-dihydro-6H-pyrrolo[3,2,1-ij]quinoline-5-carboxylic acid hydrochloride.

26. The compound of claim 4 selected from the group consisting of (+)-8-fluoro-2-(S)-methyl-9-(4-methyl-1-piperazinyl)-6-oxo-1,2-dihydro-6H-pyrrolo[3,2,1-ij]quinoline-5-carboxylic acid, (+)-8-fluoro-2-(S)-methyl-9-(4-methyl-1-piperazinyl)-6-oxo-1,2-dihydro-6H-pyrrolo[3,2,1-ij]quinoline-5-carboxylic acid hydrochloride, (+)-8-fluoro-2-(S)-methyl-9-(3,4-dimethyl-1-piperazinyl)-6-oxo-1,2-dihydro-6H-pyrrolo[3,2,1-ij]quinoline-5-carboxylicacid, (+)-8-fluoro-2-(S)-methyl-9-(3,4-dimethyl-1-piperazinyl)-6-oxo-1,2-dihydro-6H-pyrrolo[3,2,1-ij]quinoline-5-carboxylic acid hydrochloride, (+)-8-fluoro-2-(S)-methyl-9-(3,4,5-trimethyl-1-piperazinyl)-6-oxo-1,2-dihydro-6H-pyrrolo[3,2,1-ij]quinoline-5-carboxylic acid, (+)-8-fluoro-2-(S)-methyl-9-(3,4,5-trimethyl-1-piperazinyl)-6-oxo-1,2-dihydro-6H-pyrrolo[3,2,1-ij]quinoline-5-carboxylic acid hydrochloride, (+)-8-fluoro-2-(S)-methyl-9-((3S)-3,4-dimethyl-1-piperazinyl)-6-oxo-1,2-dihydro-6H-pyrrolo[3,2,1-ij]quinoline-5-carboxylic acid and (+)-8-fluoro-2-(S)-methyl-9-((3S)-3,4-dimethyl-1-piperazinyl)-6-oxo-1,2-dihydro-6H-pyrrolo[3,2,1-ij]quinoline-5-carboxylic acid hydrochloride.

27. The compound of claim 5 selected from the group consisting of (+)-8-fluoro-2-(S)-methyl-9-(3-amino-1-pyrrolidinyl)-6-oxo-1,2-dihydro-6H-pyrrolo[3,2,1-ij]quinoline-5-carboxylic acid, (+)-8-fluoro-2-(S)-methyl-9-(3-amino-1-pyrrolidinyl)-6-oxo-1,2-dihydro-6H-pyrrolo[3,2,1-ij]quinoline-5-carboxylic acid hydrochloride, (+)-8-fluoro-2(S)-methyl-9-[3-(ethylaminomethyl)-1-pyrrolidinyl]-6-oxo-1,2-dihydro-6H-pyrrolo[3,2,1-ij]quinoline-5carboxylic acid and (+)-8-fluoro-2(S)-methyl-9-[3-(isopropylaminomethyl)-1-pyrrolidinyl]-6-oxo-1,2-dihydro-6H-pyrrolo[3,2,1-ij]quinoline-5-carboxylic acid hydrochloride.

28. The compound of claim 3 selected from the group consisting of (+)-8-fluoro-2-(S)-methyl-9-(3-methyl-1-piperazinyl)-6-oxo-1,2-dihydro-6H-pyrrolo[3,2,1-ij]quinoline-5-carboxylic acid hydrochloride, (−)-8-fluoro-2-(S)-methyl-9-(3-(S)-methyl-1-piperazinyl)-6-oxo-1,2-dihydro-6H-pyrrolo[3,2,1-ij]quinoline-5-carboxylic acid hydrochloride and (+)-8-fluoro-2-(S)-methyl-9-(3-(R)-methyl-1-piperazinyl)-6-oxo-1,2-dihydro-6H-pyrrolo[3,2,1-ij]quinoline-5-carboxylic acid hydrochloride.

29. The compound of claim 4 selected from the group consisting of (+)-8-fluoro-2-(S)-methyl-9-(3,4-dimethyl-1-piperazinyl)-6-oxo-1,2-dihydro-6H-pyrrolo[3,2,1-ij]quinoline-5-carboxylic acid, (+)-8-fluoro-2-(S)-methyl-9-(3,4-dimethyl-1-piperazinyl)-6-oxo-1,2-dihydro-6H-pyrrolo[3,2,1-ij]quinoline-5-carboxylic acid hydrochloride, (+)-8-fluoro-2-(S)-methyl-9-((3S)-3,4-dimethyl-1-piperazinyl)-6-oxo-1,2-dihydro-6H-pyrrolo[3,2,1-ij]wuiniline-5-carboxylic acid and (+)-8-fluoro-2-(S)-methyl-9-((3S)-3,4-dimethyl-1-piperazinyl)-6-oxo-1,2-dihydro-6H-pyrrolo[3,2,1-ij]quinoline-5-carboxylic acid hydrochloride.

30. A pharmaceutical composition for antimicrobial use comprising a therapeutically effective amount of a pyrroloquinoline compound or salt thereof defined in claim 2, and a pharmaceutically acceptable carrier.

31. A pharmaceutical composition for antimicrobial use comprising a therapeutically effective amount of a pyrroloquinoline compound or salt thereof defined in claim 1, and a pharmaceutically acceptable carrier.

32. A pharmaceutical composition for antimicrobial use comprising a therapeutically effective amount of a pyrroloquinoline compound or salt thereof defined in claim 23 or 24, and a pharmaceutically acceptable carrier.

33. A pharmaceutical composition for antimicrobial use comprising a therapeutically effective amount of a pyrroloquinoline compound or salt thereof defined in claim 3, and a pharmaceutically acceptable carrier.

34. A pharmaceutical composition for antimicrobial use comprising a therapeutically effective amount of a pyrroloquinoline compound or salt thereof defined in claim 4, and a pharmaceutically acceptable carrier.

35. A pharmaceutical composition for antimicrobial use comprising a therapeutically effective amount of a pyrroloquinoline compound or salt thereof defined in claim 28, and a pharmaceutically acceptable carrier.

36. A pharmaceutical composition for antimicrobial use comprising a therapeutically effective amount of a pyrroloquinoline compound or salt thereof defined in claim 29, and a pharmaceutically acceptable carrier.

* * * * *